(12) United States Patent
Verbakel et al.

(10) Patent No.: US 11,224,373 B2
(45) Date of Patent: Jan. 18, 2022

(54) ADAPTER AND CONNECTION UNIT FOR COUPLING WITH MEDICAL COUPLING UNIT AND SENSOR

(71) Applicant: KONINKLIJKE PHILIPS N.V., Eindhoven (NL)

(72) Inventors: Frank Verbakel, Helmond (NL); Nicolaas Lambert, Waarle (NL); Hugo Veenstra, Kleine Brogel (BE); Marc Andre De Samber, Lommel (BE); Josephus Arnoldus Henricus Maria Kahlman, Tilburg (NL); Pierre Hermanus Woerlee, Valkenswaard (NL)

(73) Assignee: Koninklijke Philips N.V., Eindhoven (NL)

( * ) Notice: Subject to any disclaimer, the term of this patent is extended or adjusted under 35 U.S.C. 154(b) by 422 days.

(21) Appl. No.: 16/324,133

(22) PCT Filed: Aug. 14, 2017

(86) PCT No.: PCT/EP2017/070547
§ 371 (c)(1),
(2) Date: Feb. 8, 2019

(87) PCT Pub. No.: WO2018/033503
PCT Pub. Date: Feb. 22, 2018

(65) Prior Publication Data
US 2019/0175047 A1     Jun. 13, 2019

(30) Foreign Application Priority Data
Aug. 17, 2016 (EP) ..................... 16184464

(51) Int. Cl.
*A61B 5/30* (2021.01)

(52) U.S. Cl.
CPC ........ *A61B 5/303* (2021.01); *A61B 2562/225* (2013.01); *A61B 2562/227* (2013.01)

(58) Field of Classification Search
CPC ... A61B 5/1455; A61B 5/0428; A61B 5/0402; A61B 5/04028; A61B 5/04286;
(Continued)

(56) References Cited

U.S. PATENT DOCUMENTS 5,546,950 A  8/1996 Schoeckert
5,582,180 A  12/1996 Manset
(Continued)

FOREIGN PATENT DOCUMENTS

EP  1932470    6/2008
WO  2017220328  12/2017
WO  2018162616  9/2018

*Primary Examiner* — Edwin A. Leon
*Assistant Examiner* — Milagros Jeancharles

(57) ABSTRACT

The present invention relates to an adapter (100) for coupling with a medical coupling unit (1) and a medical sensor (2) that are configured for being coupled for electrical signal transmission between them. The adapter comprises an adapter coupling unit (101) configured to fit with a coupling-side connector (10) of the medical coupling unit (1) and including a plurality of coupling-side electrical contacts (111, 113) for contacting a plurality of electrical contacts (11, 13) of the coupling-side connector (10) and a sensor-side connector (120) configured to fit with a sensor-side connector (20) of the medical sensor (2) and including a plurality of sensor-side electrical contacts (121, 123) for contacting a plurality of electrical contacts (21, 23) of the sensor-side connector (20), allowing the adapter coupling unit (101) to be mechanically coupled between the medical coupling unit (1) and the medical sensor (2). Further, the adapter comprises one or more wires (102) fixedly connected to the adapter coupling unit for coupling one or more sensor elements (225) with the adapter coupling unit for (Continued)

electrical signal transmission from the one or more sensor elements to the adapter coupling unit, and connection circuitry (103) within the adapter coupling unit (101) for connecting said sensor-side electrical contacts (121, 123) and said one or more wires (102) with said coupling-side electrical contacts (111, 113) allowing signal transmission from the medical sensor (2) and one or more sensor elements (225) coupled to the adapter coupling unit (101) to the medical coupling unit (1).

13 Claims, 9 Drawing Sheets

(58) Field of Classification Search
CPC ........ A61B 2562/225; A61B 2562/227; G01D 21/00; H01R 13/64; H01R 27/02; H01R 31/06
USPC .................................. 439/628, 638, 639, 909
See application file for complete search history.

(56) References Cited

U.S. PATENT DOCUMENTS

| | | | |
|---|---|---|---|
| 5,813,979 A | 9/1998 | Wolfer | |
| 6,086,430 A * | 7/2000 | Amoni | H01R 13/645 |
| | | | 439/639 |
| 6,349,228 B1 * | 2/2002 | Kiani | A61B 5/14551 |
| | | | 600/323 |
| 7,270,568 B2 | 9/2007 | Osypka | |
| 7,618,377 B2 * | 11/2009 | McAtamney | A61B 5/301 |
| | | | 600/508 |
| 7,633,560 B1 | 12/2009 | Sivertsen | |
| 7,675,190 B1 | 3/2010 | Muller | |
| 8,568,160 B2 * | 10/2013 | Coggins | A61B 5/303 |
| | | | 439/502 |
| 8,668,651 B2 | 3/2014 | Burnes | |
| 8,897,865 B2 * | 11/2014 | Farrior | A61B 5/318 |
| | | | 600/522 |
| 9,072,444 B2 | 7/2015 | Burnes | |
| 9,198,589 B2 | 12/2015 | Chou | |
| 9,204,794 B2 * | 12/2015 | Lisogurski | A61M 16/0459 |
| 9,226,678 B1 * | 1/2016 | Ghaffari | A61B 5/25 |
| 9,226,679 B2 | 1/2016 | Balda | |
| 9,456,761 B2 | 10/2016 | Elschenbroich | |
| 9,461,393 B2 * | 10/2016 | Carley | A61B 5/303 |
| 9,734,358 B2 * | 8/2017 | Soffer | H01R 13/7175 |
| 10,008,817 B2 * | 6/2018 | Fullerton | H01R 13/6675 |
| 10,802,046 B2 * | 10/2020 | Kirst | G01R 1/0416 |
| 2002/0060617 A1 | 5/2002 | Walbeck | |
| 2005/0009404 A1 * | 1/2005 | Lee | H01R 31/06 |
| | | | 439/638 |
| 2007/0099487 A1 | 5/2007 | Osypka | |
| 2008/0132106 A1 | 6/2008 | Burnes | |
| 2012/0295473 A1 | 11/2012 | Chen | |
| 2012/0320546 A1 | 12/2012 | Wu | |
| 2014/0049292 A1 * | 2/2014 | Popescu | G02B 6/43 |
| | | | 327/100 |
| 2016/0170928 A1 * | 6/2016 | Tamarkin | G06F 13/409 |
| | | | 710/313 |
| 2017/0222459 A1 * | 8/2017 | Kang | H01R 31/065 |
| 2018/0145469 A1 * | 5/2018 | Chung | H04M 1/02 |
| 2019/0131742 A1 * | 5/2019 | Veenstra | H01R 13/64 |
| 2020/0339265 A1 * | 10/2020 | Yilmaz | H01R 25/006 |

* cited by examiner

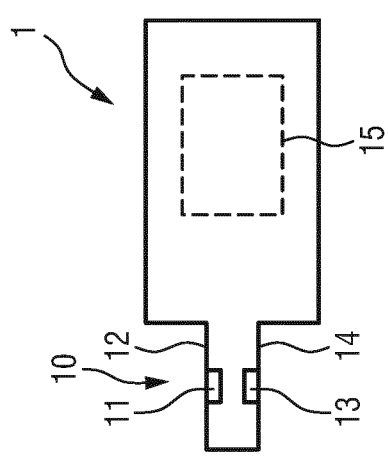
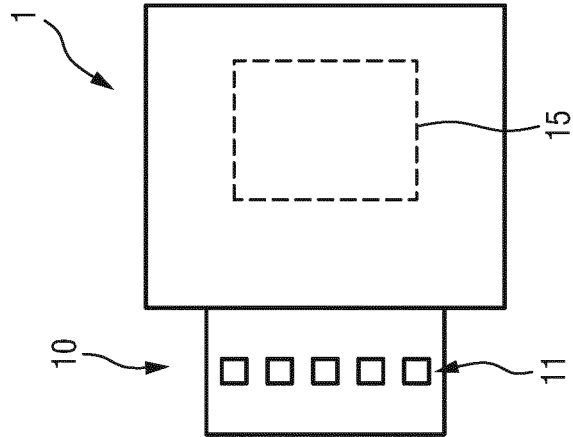
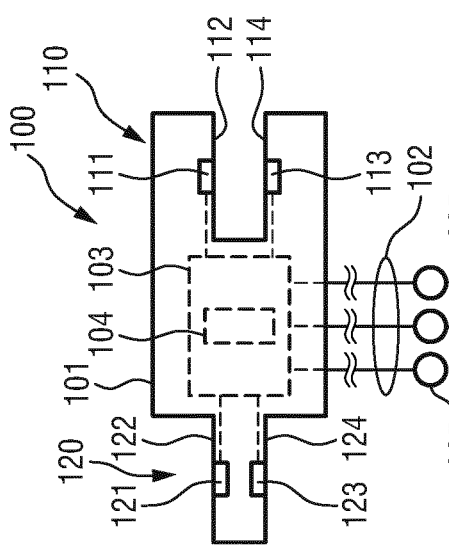
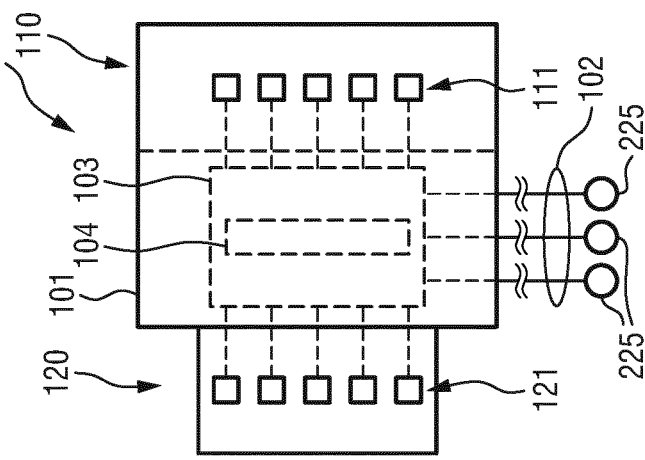
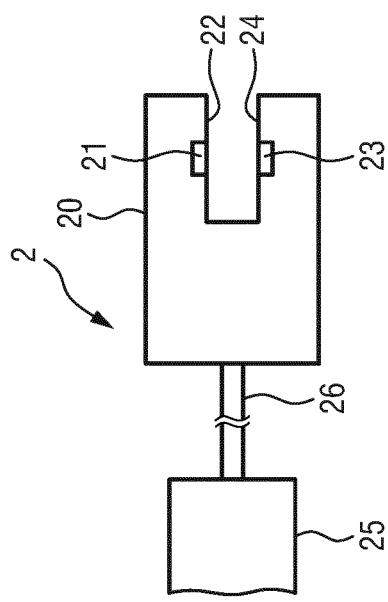
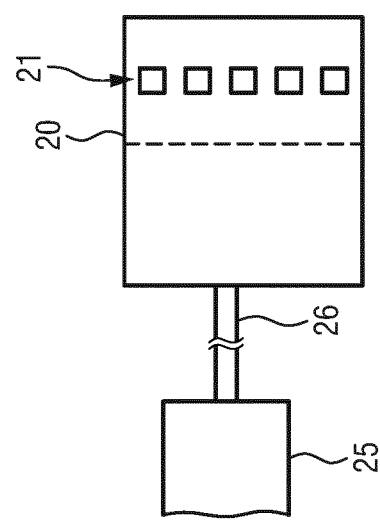

ADAPTER AND CONNECTION UNIT FOR COUPLING WITH MEDICAL COUPLING UNIT AND SENSOR

CROSS REFERENCE TO RELATED APPLICATIONS

This application is the U.S. National Phase application under 35 U.S.C. § 371 of International Application No. PCT/EP2017/070547 filed Aug. 14, 2017, published as WO 2018/033503 on February 22, 108, which claims the benefit of European Patent Application Number 16184464.2 filed Aug. 17, 2016. These applications are hereby incorporated by reference herein.

FIELD OF THE INVENTION

The present invention relates to an adapter for coupling with a medical coupling unit and a medical sensor that are configured for being coupled for electrical signal transmission between them. The present invention relates further to a connection unit for connecting two or more medical coupling units with two or more medical sensors for electrical signal transmission between them.

BACKGROUND OF THE INVENTION

Vital signs monitoring equipment are commonly used in healthcare. Vital signs that are frequently monitored include the electrocardiogram (ECG), concentration of oxygen in the blood (SpO2), respiration, blood pressure (invasive: IBP, non-invasive: NIBP) and temperature. Depending on the application, patient status and required monitoring and follow-up and care setting, requirements for the measurement differ on aspects such as accuracy, power dissipation, features, etc. An example monitor for use in hospitals is the commercially available Philips IntelliVue MP30. The apparatus works with plug-in measurement server units and is intended for in-hospital use, where the patient remains in the bed. A dedicated connector is provided for each different sensor that is plugged in for each of the parameters to be monitored.

There are various scenarios and medical conditions where vital signs of the patient need to be monitored and for which specific monitors have been developed. For example, the commercially available Philips IntelliVue MX40 offers better mobility to the patient. It has a dedicated connector and cable, which connect to the top side of the monitor.

For the near future it is anticipated that new monitoring platforms will be developed that can be used across the continuum of care. For good patient comfort, such a next-generation module must be wearable, lightweight, body conformal, non-obtrusive and small. Furthermore, for patient comfort, re-wiring and replacement of electrodes should be avoided as much as possible. This introduces challenges to the connections. Hence, there is a need for providing a medical connector design in support of such a new monitoring platform.

Further, there is a strong trend towards wearable devices in healthcare and/or lifestyle. This is related among others to increasing demand for ambulatory monitoring ease-of-use, patient comfort, workflow management, etc. One of the key characteristics and requirements of such wearable device is its form factor, for which ECG is challenging to meet. For instance, up to 10 electrodes and physical wires (often called leadwires or leads in the field of ECG) are required to generate a 12 lead ECG representation on the monitor.

Conventionally, a trunk cable is used as an interface between lead sets comprising 3, 4, 5 or 6 electrodes and the ECG monitor. If a 5 lead ECG configuration needs to be extended to a 12 lead ECG (10 wires), two leadwire sets, a limb set and a chest set, are combined. The 12-lead trunk cable is over-dimensioned when used for a 5 lead ECG measurement, as to allow for this extension option. Moreover, when a 5 L measurement is followed by a 12 L measurement, all leadwires to the patient are replaced. This is because the 12 L leadset comes with a full set of new leadwires. Protection elements such as resistors are typically embedded in the trunk cable connector and need to support operation of 12 lead configurations. The protection resistors are large and expensive and it is thus not attractive to over-dimension the trunk cable.

U.S. Pat. No. 9,198,589 B2 discloses an ECG data acquisition system, including a main housing, at least two electrodes, an ECG signal acquisition circuitry having a processor and a memory for storing acquired data, a connector for communication, and a movable housing, covering the connector and having at least an electrode mounted thereon. As executing the ECG signal acquisition, the movable housing is in a first state, and as communicating with an external equipment, the movable housing is moved to a second state for exposing the connector and electrically disconnecting the electrode thereon from the ECG signal acquisition circuitry.

EP 1 932 470 A1 discloses a method for coupling an ECG monitor with an incompatible ECG lead set including the steps of providing an ECG adapter including an adapter body having at least one monitor connector adapted for coupling to an input of an ECG monitor and at least one lead set receptacle adapted for coupling to a connector of an ECG lead set incompatible with the input of the ECG monitor, coupling the at least one monitor connector of the adapter body with the input of the ECG monitor and coupling the at least one lead set receptacle of the adapter body with the connector of the ECG lead set to thereby electrically couple the ECG lead set with the ECG monitor.

SUMMARY OF THE INVENTION

It is an object of the present invention to reduce the size of the ECG measurement lead sets/trunk cable.

In a first aspect of the present invention an adapter is presented comprising:
- an adapter coupling unit comprising a coupling-side connector configured to fit with a coupling-side connector of the medical coupling unit and including a plurality of coupling-side electrical contacts for contacting a plurality of electrical contacts of the coupling-side connector and a sensor-side connector configured to fit with a sensor-side connector of the medical sensor and including a plurality of sensor-side electrical contacts for contacting a plurality of electrical contacts of the sensor-side connector, allowing the adapter coupling unit to be mechanically coupled between the medical coupling unit and the medical sensor,
- one or more wires fixedly connected to the adapter coupling unit for coupling one or more sensor elements with the adapter coupling unit for electrical signal transmission from the one or more sensor elements with the adapter coupling unit, and
- connection circuitry within the adapter coupling unit for connecting said sensor-side electrical contacts and said one or more wires to said coupling-side electrical contacts allowing signal transmission from the medical sensor and one or more sensor elements coupled to the adapter coupling unit to the medical coupling unit.

In a second aspect of the present invention a connection unit is presented comprising:

- a first coupling-side connector including a plurality of coupling-side electrical contacts for contacting a plurality of electrical contacts of a first coupling-side connector of a first medical coupling unit and
- a second coupling side connector including a plurality of coupling-side electrical contacts for contacting a plurality of electrical contacts of a second coupling-side connector of a second medical coupling unit.

The present invention is based on the idea to omit the bulky conventionally used trunk cable connector. According to one aspect of the present invention the lead sets (i.e. the one or more wires) are directly connected via the proposed adapter to a medical coupling unit, e.g. to a measurement module or a patient monitor, to which adapter is coupled via the coupling-side connector (which may thus also be called "monitoring-side connector"). The conventional approach of combining multiple lead sets in one is thus no longer necessary and the leadset and adapter can be selected according to the present use case. The proposed adapter can thus e.g. be used to extend a 3 or 5 lead ECG to a 12 lead ECG configuration and thus allows re-using existing electrode connections and wires. This avoids the need for an over-dimensioned trunk cable, thereby reducing the size and weight of the unit the patient is usually carrying.

Further, while conventionally the protection circuitry, e.g. protection resistors and/or sidactors (clamps), are located in the trunk cable connector (i.e. the resistors) and/or the ECG monitor (i.e. the sidactors), according to a preferred embodiment of the present invention, particularly in case of using the adapter in connection with a sensor-side connector with an ECG leadset, the protection circuitry generally required for ECG such as protection resistors and the sidactors, can be arranged in the adapter.

Hence, the adapter is configured such that it fits—electrically and mechanically—between the medical sensor and the medical coupling unit (e.g. of a patient monitor), i.e. the functions of the medical sensor and the medical coupling unit are not influenced by the adapter. The medical sensor and the medical coupling unit can thus be used with or without the adapter without loss of functionality and generally without the need for any (electrical or mechanical) modifications.

Moving the connector extensibility from the bulky, unprotected, high voltage trunk connector (which has to withstand 5 kV defibrillation shocks) to the smaller, protected, lower voltage adapter leads to a reduction in size for two reasons: The bulky trunk cable connector is omitted and the proposed adapter only needs to protect (in case of use with ECG) the (e.g. 3 to 5) wires, but not the full set of wires (e.g. the 12 wires). This reduces the number of bulky protection resistors and protection elements (sidactors, etc.) to the number required in the actual configuration, and no unused protection elements are present, avoiding over-dimensioning.

Generally, the adapter can not only be used to extend an ECG set of leads, but can also be used with other sensors, e.g. an SpO2 sensor and thus supports several measurements including ECG (e.g. up to 12-Lead) and SpO2. For instance, an existing ECG leadset can be extended by an SpO2 sensor using the adapter to combined ECG and SpO2 measurements. Further examples are that the adapter is used to extend any single medical transducer (thermometer, invasive blood pressure transducer, etc.) by another one, or even to replace the wiring of an auxiliary transducer (e.g. accelerometer for motion artifacts, posture and/or respiration) by extra ECG leads.

The proposed solution further avoids open contacts or dangling wires. The adapter not only needs to provide connectivity to the extra leads, but also links the common shield and protection reference contact. Conventionally, this is achieved by deeply recessed electrical contacts and a mechanical protection cap that the user can remove. According to the proposed solution the medical sensor is first detached from the medical coupling unit (e.g. a monitor connector) and then the adapter is put in between. This may imply a loss of signals for a few (e.g. 2 or 3) seconds, which is considered acceptable in all regular use cases.

According to an embodiment said plurality of coupling-side electrical contacts comprises a plurality of first coupling-side electrical contacts in or on a first surface and a plurality of second coupling-side electrical contacts in or on a second surface opposite the first surface and said plurality of sensor-side electrical contacts comprises a plurality of first sensor-side electrical contacts in or on a first surface and a plurality of second sensor-side electrical contacts in or on a second surface opposite the first surface. Thus, a generic adapter is provided with a limited number of (generic) connections so that it can be coupled to various medical sensors and medical coupling units.

In one embodiment said plurality of coupling-side electrical contacts are configured as male contacts and said plurality of sensor-side electrical contacts are configured as female contacts, whereas in another embodiment said plurality of coupling-side electrical contacts are configured as female contacts and said plurality of sensor-side electrical contacts are configured as male contacts. Hence, the contacts may generally be configured as plug or as socket, depending on the configuration of the corresponding connectors of the sensor and the medical coupling unit.

The protection circuitry may comprise one or more sidactors and/or protection resistors coupled between the one or more sensor elements and the one or more coupling-side electrical contacts. This saves space and avoids over-dimensioning as explained above.

The adapter coupling unit may generally have any mechanical design and form factor as needed. In preferred embodiments it has a flat or cylindrical shape.

Some of the conventionally used connectors of the sensor may be swappable, i.e. can be connected to the conventionally used trunk cable in different orientations. With this particular swappable solution an additional mechanism is preferably provided to prevent mishaps when an adapter is added, i.e. said coupling-side connector and/or said sensor side connector comprises one or more mechanical keying elements. Adding an adapter to a regular non-swappable connector of the sensor or medical coupling unit poses no such additional problems: all the connector mechanics and measurement electronics can stay unmodified.

According to another preferred embodiment said adapter coupling unit comprises communication circuitry for communication with the medical coupling unit and/or a medical sensor. This may e.g. enable mutual recognition and/or identification of the adapter, the medical coupling unit and/or a medical sensor.

There are various constructional solutions for the wires of the adapter. In one embodiment the one or more wires may extend from one or two side surfaces of the adapter coupling unit. Thus, these wires do not cross with the wires of the sensor-side connector. For instance, said one or more wires extend from one or two side surfaces of the adapter coupling unit at an angle of 90° with respect to the respective side surface.

According to another embodiment said adapter coupling unit is larger in width than the sensor-side connector of the medical sensor, wherein said one or more wires extend from a protruding portion of the adapter coupling unit, which protrudes beyond the sensor-side connector, in a direction of the sensor-side connector. This solution may be more space-saving.

According to a second aspect of the present invention a connection unit is used to increase from e.g. a 5 lead to a 12 lead ECG. Two coupling-side connectors of two medical coupling units (modules) capable of e.g. a 5 lead ECG each are combined by the connection unit to produce e.g. a 12 lead capable combined module. The connections needed between the two modules are provided by the connection unit. In this way the bulky trunk cable can also be omitted.

In an embodiment said first coupling-side connector and said second coupling-side connector are arranged on top of each other. Hence, the two medical coupling units are also arranged on top of each other and are connected at one of their front surfaces via the first and second coupling-side connectors.

The connection unit may further comprise a first sensor-side connector including a plurality of sensor-side electrical contacts for contacting a plurality of electrical contacts of a first sensor-side connector of a first medical sensor unit and a second sensor side connector including a plurality of sensor-side electrical contacts for contacting a plurality of electrical contacts of a second sensor-side connector of a second medical sensor unit, wherein the first sensor-side connector is arranged opposite the first coupling-side connector and the second sensor-side connector is arranged opposite the second coupling-side connector. This provides another space-saving solution to avoid a trunk cable.

BRIEF DESCRIPTION OF THE DRAWINGS

These and other aspects of the invention will be apparent from and elucidated with reference to the embodiment(s) described hereinafter. In the following drawings FIGS. 1A-1D show a first embodiment of an adapter according to the present invention in a cross-sectional side view (FIG. 1A), a top view (FIG. 1B), a front view (FIG. 1C) and a rear view (FIG. 1D)

DETAILED DESCRIPTION OF THE EMBODIMENTS

In the following a plurality of different embodiments of the proposed adapter will be explained, mainly with reference to an application in the field of ECG using leadwires for signal transmission. The invention is, however, not limited to application in the field of ECG and to the use of leadwires. Hence, any mentioning of leadwires in this context shall be understood as use of wires in general.

Figure 1C:
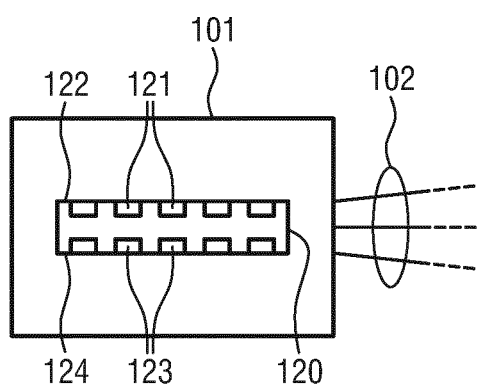
Figure 1D:
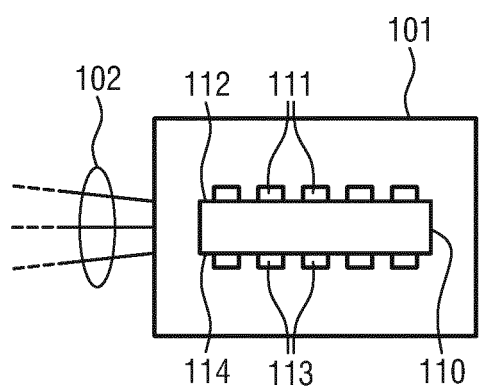

FIGS. 1A-1D show a first embodiment of an adapter 100 according to the present invention. The adapter 100 is configured for coupling with a medical coupling unit 1 and a medical sensor 2 that are configured for being coupled for electrical signal transmission between them. Various views are shown including a cross-sectional side view (FIG. 1A), a top view (FIG. 1B), a front view (FIG. 1C) and a rear view (FIG. 1D).

The medical coupling unit 1 comprises a coupling-side connector 10 comprising a plurality of first electrical (i.e. galvanic) contacts 11 in or on a first surface 12 (preferably along a first row) and a plurality of second electrical contacts 13 in or on a second surface 14 (preferably along a second row; in other embodiments other mechanical constructions may be used, e.g. a single row only or several rows, or other arrangements) opposite the first surface 12. Optionally, the medical coupling unit 1 may comprise a connector interface 15 for analyzing electrical signals available at one or more of the plurality of first and second electrical contacts 11, 13 to detect one or more of presence of a medical sensor 2 coupled to the medical coupling unit 1, the type of medical sensor 2 coupled to the medical coupling unit 1, and the orientation of a sensor-side connector 20 of a medical sensor 2 coupled to the medical coupling unit 1.

The sensor 2 comprises a sensor-side connector 20 comprising a plurality of first electrical contacts 21 in or on a first surface 22 (preferably along a first row) and a plurality of second electrical contacts 23 in or on a second surface 24 (preferably along a second row) opposite the first surface 22. Further, the sensor 2 comprises a sensor unit 25 for sensing a desired measurement parameter and/or generating electrical signals to drive actuators. The sensor unit 25 is coupled to the sensor-side connector 20 e.g. via a cable 26.

In the embodiment shown in FIGS. 1A-1D, the coupling-side connector 10 is configured as plug (i.e. male connector), in which the first electrical contacts 11 are arranged on the top surface 12 of the plug and the second electrical contacts 13 are arranged on the bottom surface 14 of the plug. The sensor-side connector 20 is configured as corresponding socket (i.e. female connector) for insertion of the plug, wherein the first electrical contacts 21 are arranged in or on an upper surface 22 of the socket and the second electrical contacts 23 are arranged in or on a lower surface 24 of the socket. In other embodiments the coupling-side connector may be configured as socket and the sensor-side connector may be configured as corresponding plug. Further, the number of electrical contacts may differ from the number of contacts in the embodiment shown in FIGS. 1A-1D. The sensor 2 may generally be any sensor for sensing a patient's vital sign, such as an ECG sensor, an SpO2 sensor, a blood pressure sensor (IBP—invasive blood pressure; NIBP—non-invasive blood pressure), a temperature sensor, etc. In case of an ECG sensor, the sensor unit 25 comprises a plurality of sensor elements connected to the sensor-side connector 20 via separate cables 26 (e.g. leadwires in case of ECG or generally wires).

The sensor 2 may be directly connected to the coupling-side connector 10 or via the adapter 100, i.e. the adapter can be inserted between the sensor 2 and the coupling-side connector 10, as shown in FIGS. 1A-1D. It should be noted that when contacts from different measurements are combined into one connector the creepage and clearance distances need to be dimensioned such that the medical safety regulations for measurement to measurement isolation are met.

The adapter 100 comprises an adapter coupling unit 101 comprising a coupling-side connector 110 configured to fit with the coupling-side connector 10 of the medical coupling unit 1 and including a plurality of coupling-side electrical contacts 111, 113 for contacting a plurality of electrical contacts 11, 13 of the coupling-side connector 10 and a sensor-side connector 120 configured to fit with a sensor-side connector 20 of the medical sensor 2 and including a plurality of sensor-side electrical contacts 121, 123 for contacting a plurality of electrical contacts 21, 23 of the sensor-side connector 20, allowing the adapter coupling unit 101 to be mechanically coupled between the medical coupling unit 1 and the medical sensor 2.

In this embodiment of the adapter the plurality of coupling-side electrical contacts 111, 113 comprises a plurality of first coupling-side electrical contacts 111 in or on a first surface 112 and a plurality of second coupling-side electrical contacts 113 in or on a second surface 114 opposite the first surface and the plurality of sensor-side electrical contacts 120 comprises a plurality of first sensor-side electrical contacts 121 in or on a first surface 122 and a plurality of second sensor-side electrical contacts 123 in or on a second surface 124 opposite the first surface.

Further, in this embodiment the plurality of coupling-side electrical contacts 111, 113 are configured as female contacts and the plurality of sensor-side electrical contacts 121, 123 are configured as male contacts. In another embodiment the plurality of coupling-side electrical contacts 111, 113 are configured as female contacts and the plurality of sensor-side electrical contacts 121, 123 are configured as male contacts.

The adapter coupling unit 101 is hence configured such that it fits mechanically between the coupling-side connector 10 and the sensor-side connector 20, which are—if no adapter 100 is used—mechanically coupled directly or via a trunk cable.

The adapter 100 further comprises one or more leadwires 102 connected to the adapter coupling unit 101 for coupling one or more sensor elements 225 with the adapter coupling unit 101. The one or more sensor elements 225 are configured for sensing a desired measurement parameter and/or generating corresponding electrical signals, which are transmitted from the one or more sensor elements 225 to the adapter coupling unit 101. The one or more sensor elements 225 may generally be configured and of the same type as the sensor unit 25 of the sensor 2. For instance, a number of ECG electrodes (sensor elements 225) may be connected to the adapter coupling unit 101 via separate leadwires 102.

The adapter 100 further comprises connection circuitry 103 within the adapter coupling unit 101 for connecting said sensor-side electrical contacts 121, 123 and said one or more leadwires 102 with said coupling-side electrical contacts 111, 113. Said connection circuitry 103 may comprise wiring to combine the different contacts and leadwires appropriately, as will be explained below in more detail. Said connection circuitry allows signal transmission from the medical sensor and one sensor elements coupled to the adapter coupling unit to the medical coupling unit, i.e. via the adapter signals can be transferred from the medical sensor and from additional sensor elements connected to the adapter to the medical coupling unit of e.g. a patient monitor. Optionally, signals can be exchanged bidirectionally, allowing e.g. a patient monitor to control the medical sensor and sensor elements.

The adapter 100 may further comprise protection circuitry 104, preferably within the adapter coupling unit 101, e.g. as part of the connection circuitry 103, particularly in case of using the adapter in the field of ECG. A further aspect relating to the whole arrangement including the adapter is safety and protection. Since embodiments of the medical coupling unit optionally support the full continuum of care, they may be configured to meet the safety and protection requirements even while the patient is undergoing defibrillation treatments. The input network of an ECG front-end usually has multiple protective elements. These can now be arranged at least partly in the adapter.

The medical coupling unit 1 and the adapter 100 may support several measurements including ECG (e.g. up to 12-Lead) and SpO2. In contrast to conventional monitors in use today, the different measurements and sensors can share a single coupling-side connector, wherein the number of connections can be extended by use of the adapter. However, only one measurement may be performed at a time. Depending on the measurement to be performed, the corresponding sensors and/or transducers are connected to the medical coupling unit 1 via the coupling-side connector 10 either directly or (indirectly) via the adapter 100.

Figure 2:
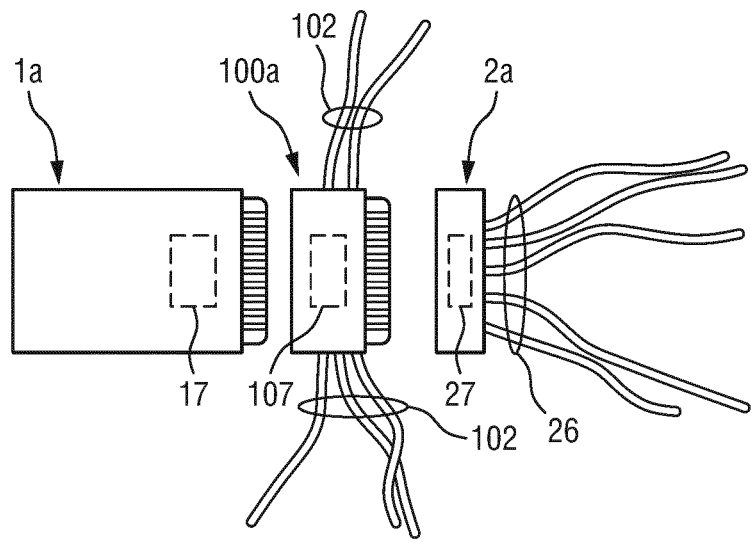
FIG. 2 shows a first practical implementation of a medical coupling unit, a sensor and an adapter, all having a flat design.
Figure 3:
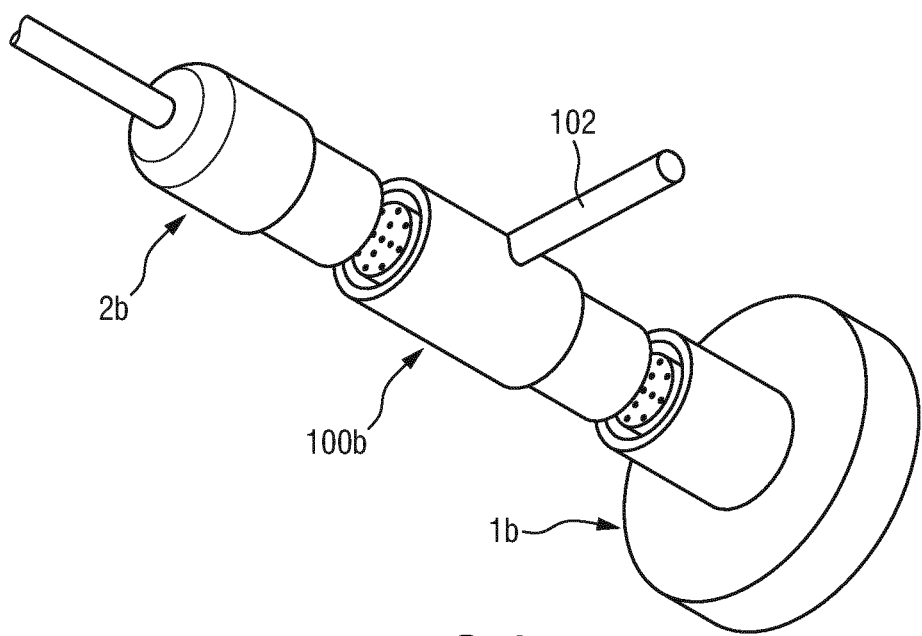
FIG. 3 shows a second practical implementation of a medical coupling unit, a sensor and an adapter, all having a cylindrical design.

FIG. 2 schematically shows a first practical implementation of a medical coupling unit 1a, a sensor 2a and an adapter 100a, all having a flat design. FIG. 3 schematically shows a second practical implementation of a medical coupling unit 1b, a sensor 2b and an adapter 100b, all having a cylindrical design, as conventionally applied using an ECG monitor connector or other analog ECG connectors.

In both embodiments an ECG module can be upgraded from 3 or 5 lead ECG to a 12 lead ECG, i.e. the number of attached leadwires can be increased from 3 or 5 to 10. This increase in leadwires makes it possible to measure 12 lead ECG without the need to replace the existing and attached 3 or 5 lead set on the patient.

The recognition of the correct combination of the extensions (i.e. the correct coupling to and with the adapter) can be made mechanical or electronical. For electronical recognition, a communication circuitry 107, e.g. an EEPROM, for communication with the medical coupling unit and/or a medical sensor, may be provided in the adapter, and also in the medical coupling unit and/or the medical sensor a corresponding communication unit 17, 27 may be provided as schematically illustrated in FIG. 2. Preferably, the communication circuitry 107 can communicate with the sensor and/or medical coupling unit via one or more dedicated pins and is used for connector/adapter identification. This ensures that only for a valid combination an ECG is recorded and/or displayed, else an error message can be reported, e.g. on the patient monitor to which the signals are transmitted.

For the mechanical recognition the coupling-side connector and/or said sensor-side connector comprises one or more mechanical keying elements preventing the wrong use (and orientation) of the adapter and the original lead set of the sensor. This ensures, for instance, that with a 3 wire lead set only a 3-to-12 lead set extender (adapter) can be used, while for the 5 wire lead set only a 5-to-12 lead set extender (adapter) is possible.

In practical application scenarios and systems there may be a large variety of embodiments of different coupling-side connectors, sensor-side connectors and corresponding connectors of the sensor and the medical coupling unit. For instance, different designs and positions of keying elements may be used to both protect against bad connector/adaptor/electronics combinations (or allowing certain combinations) while still allowing (or preventing) 180° flips. Examples of such keying elements may include slits, grooves, protrusions, etc.

Figure 4A:
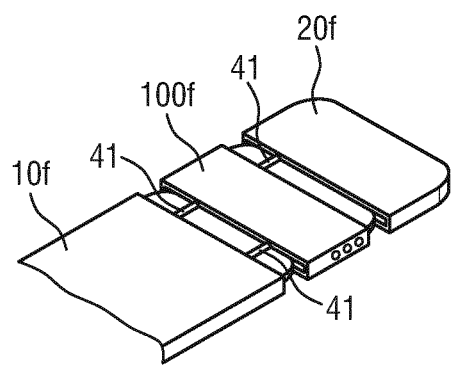
FIGS. 4A-4C show further embodiments of connectors with keying elements.
Figure 4B:
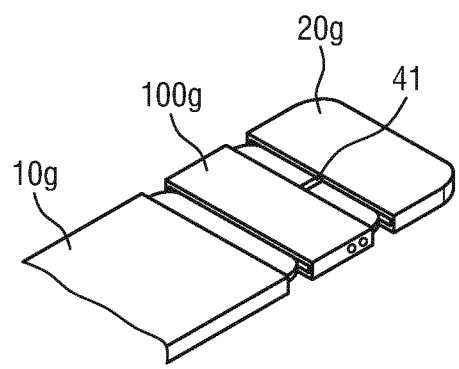
Figure 4C:
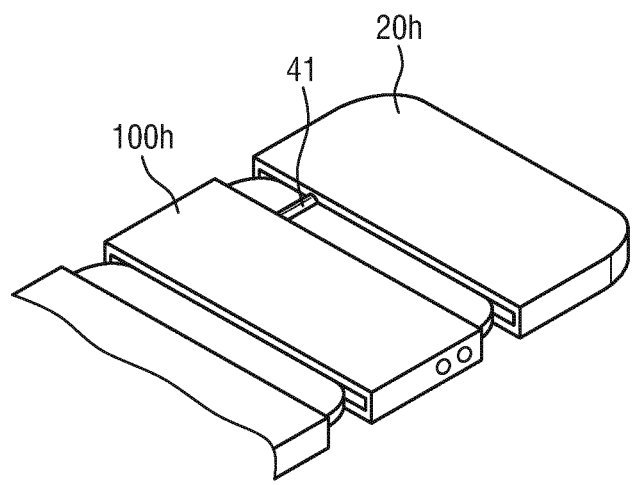

FIG. 4 shows various embodiments of coupling side connectors 10f, 10g, sensor-side connectors 20f, 20g, 20h and adapters 100f, 100g, 100h with keying elements as mechanical locks, which ensure the correct use of the adapter. In FIG. 4A a slit 41 is used to ensure the correct position of the adapter 100f. The location of these slits may differ between the 3-to-12 and 5-to-12 lead set extender. In FIG. 4B a similar function is realized by pin recognition, while in FIG. 4C key-hole recognition is used.

Figure 5:
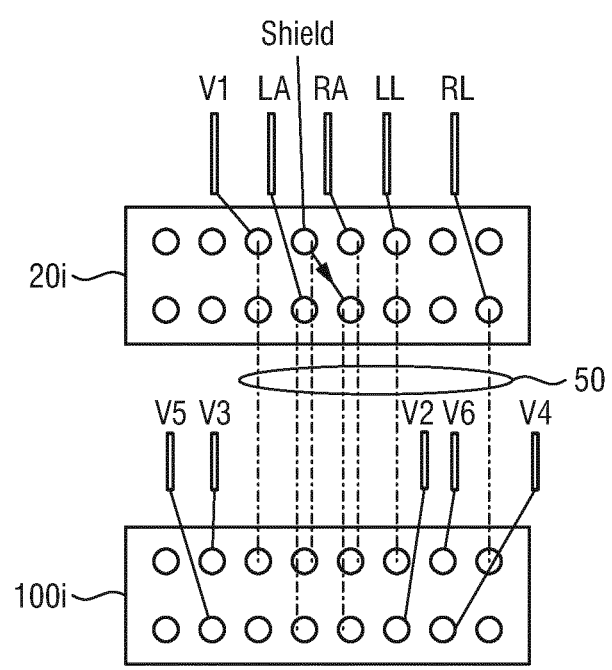
FIG. 5 shows an exemplary pin layout of the sensor-side connector and the adapter.
Figure 6:
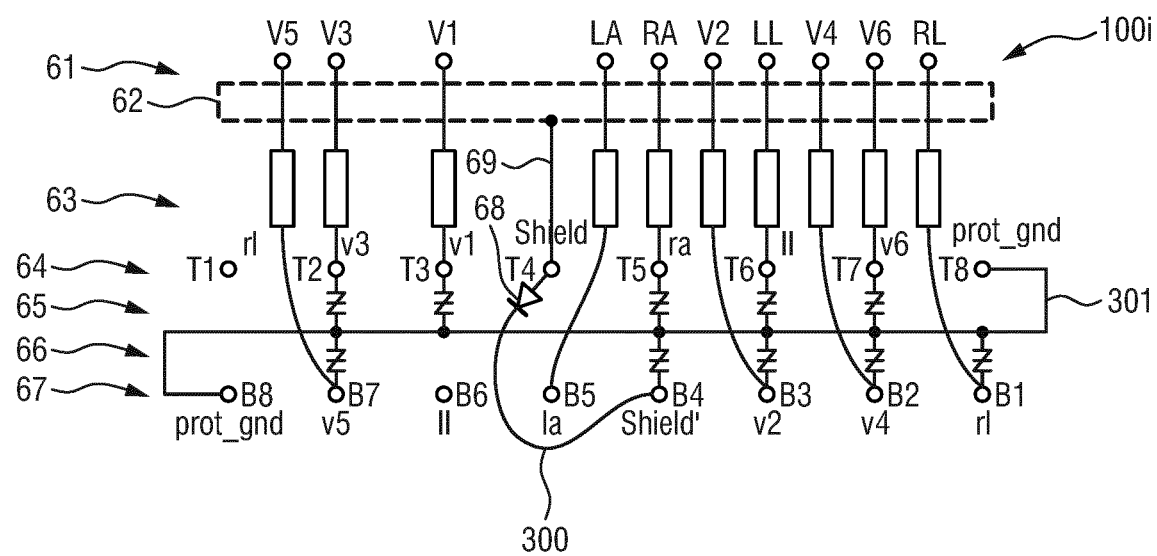
FIG. 6 shows an embodiment of the internal connections and protection elements within the adapter.
Figure 7A:
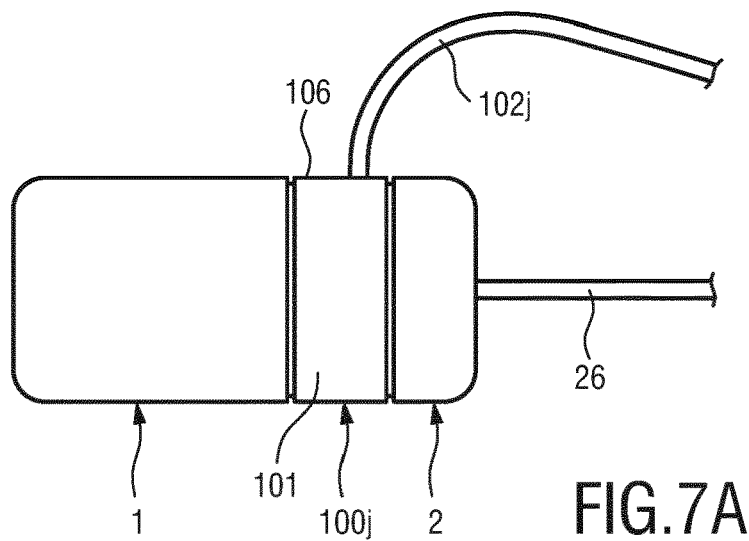
FIGS. 7A-7D show further embodiments of the adapter with different arrangements of the leadwires.
Figure 7B:
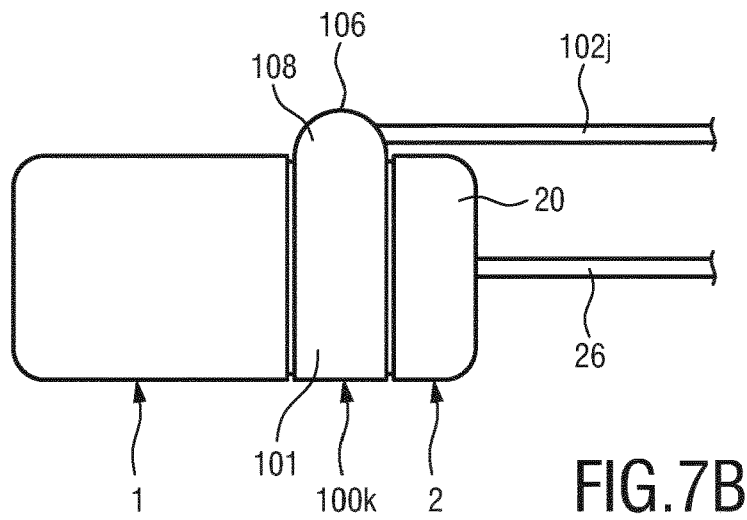
Figure 7C:
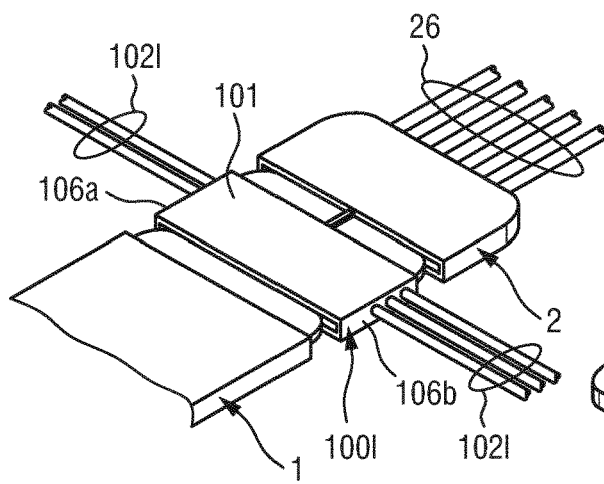
Figure 7D:
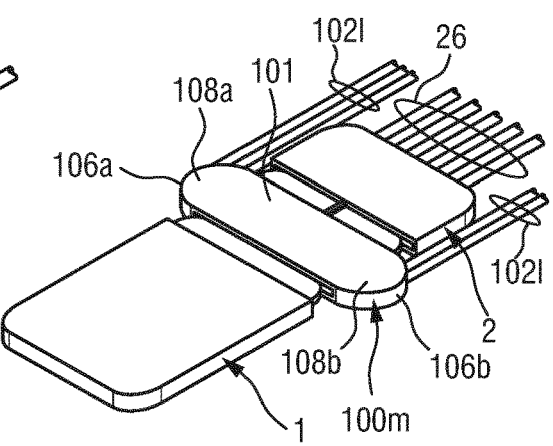

FIG. 5 shows an exemplary pin (i.e. contact) layout of the sensor-side connector 20i of a 5 lead ECG sensor and of another embodiment of an adapter 100i, each comprising 2×8 pins. FIG. 6 shows an embodiment of the internal connections within the adapter 100i representing part of the connection circuitry 103. With an increased number of pins and the accompanying electronics it is possible to have both the adapter 100i and the connector 20i free swappable. However for simplicity it is proposed in an embodiment to have only the adapter 100i swappable and to have the connector 20i attached to the adapter 100i in only one manner. This can e.g. be ensured by use of means described above with reference to FIG. 4. The dashed lines 50 in FIG. 5 are the connections passed through the adapter 100i as shown in FIG. 6.

FIG. 6 particularly shows electrode connections 61, a shielded cable 62, protection resistors 63, first contacts 64 (sensor-side connector to coupling unit), sidactors 65, 66, and second contacts 67. Further, a diode 68, a shield connection (or shield contact) 69 and one or more internal connections 300, 301 for point symmetrically connecting one or more first electrical contacts with the respective second electrical contact are provided, wherein the contact 301 serves as reference contact. The resistors 63 and the sidactors 65, 66 generally serve as protection circuitry.

Nodes with identical names are electrically shorted inside the connector 100i (e.g. rl-rl, prot_gnd-prot_gnd and ll-ll). The duplicate prot_gnd connections ensure that the protection reference is always connected between the medical coupling unit and cable, regardless the connector orientation. The duplicate rl connection ensures that the RL electrode is always connected to the medical coupling unit, regardless the connector orientation. The diode between connector pins Shield' and Shield is included to enable sensor-side connector presence detection and function selection by an optional measurement control unit or the connector interface 15, as will be detailed below. Other pin assignments are also possible. For example, the unipolar lead connections can be interchanged without any impact on functionality, as long as the assignment is known to the connector interface 15.

Considering the connector design depicted in FIG. 6 in a 1-Lead ECG application, the impact of ECG connector orientation shall be described. Signals RA, LA that together form the 1-Lead ECG signal may always be applied to a connector interface, but depending on the sensor-side connector orientation they may be swapped. It is thus provided that the connector interface detects the connector orientation, as will be described below. A 3-Lead ECG also involves electrode LL. This electrode signal is found on duplicate pins (B6 and T6) and is thus available to the connector interface on the same input, regardless of the sensor-side connector orientation. Extensions to 5-Lead and other configurations, up to 12-Lead, involve additional electrode signals that are available at only a single connector pin. Thus, the sensor-side connector orientation should be known for proper operation.

It should be noted that in FIG. 6 notations provided e.g. at electrode connections 61 with capital letters (e.g. "RL") shall indicate a particular signal at a connection on the sensor side, whereas notations provided with small letters (e.g. "rl") shall indicate the same signal as provided at a contact of the sensor-side connector, e.g. in FIG. 6 behind the protection resistor 63.

Different embodiments of the arrangement of leadwires at the adapter are shown in FIG. 7. In FIG. 7A a single cable 102j (containing all leadwires) exits the adapter 100j to the side at an angle of 90° with respect to the side surface 106 of the adapter 100j. In FIG. 7B the side surface 106 of the adapter 100k is curved and the adapter coupling unit 101 is larger in width than the sensor-side connector 20 of the medical sensor 2 so that the single cable 102j exits the adapter 100k in a direction to the front side so that it is substantially parallel to the cable 26 of the sensor 2. The cable 102j thus extends from a protruding portion 108 of the adapter coupling unit 101, which protrudes beyond the sensor-side connector 20, in a direction of the sensor-side connector 20. In FIGS. 7C and 7D the single leadwires 102l exit the adapter 100l, 100m, in these embodiments from two opposite side surfaces 106a, 106b of protruding portions 108a, 108b. In FIG. 7C the leadwires 102l exit to the side, and in FIG. 7D the leadwires 102l exit to the front. The preferred choice of the kind of cable and its arrangement mainly depends on the use case.

FIG. 8 shows different embodiments of a connection unit for connecting two or more medical coupling units 1, 1' with two or more medical sensors 2, 2' for electrical signal transmission between them. This approach can be used to increase from e.g. 5 lead to a 12 lead ECG. This embodiment use two medical coupling units 1, 1', each capable of 5 lead ECG, which are combined to produce a 12 lead capable medical coupling unit. The connections needed between the two medical coupling units 1, 1' are provided by the connection unit 200, 200a or 200b.

Figure 8A:
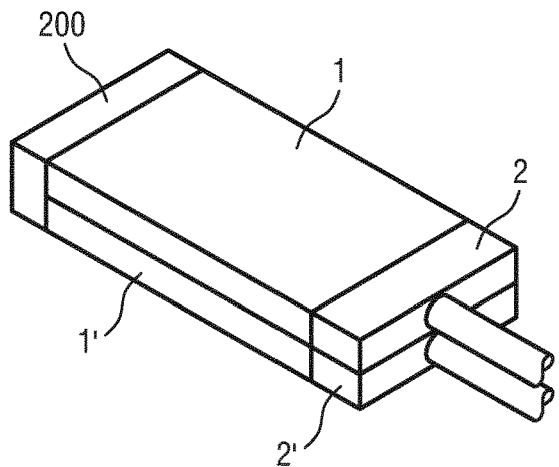
FIGS. 8A-8C show different embodiments of a connection unit for connecting two or more medical coupling units with two or more medical sensors.
Figure 8B:
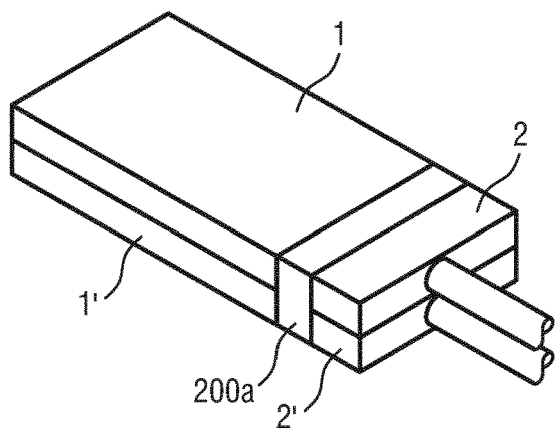
Figure 8C:
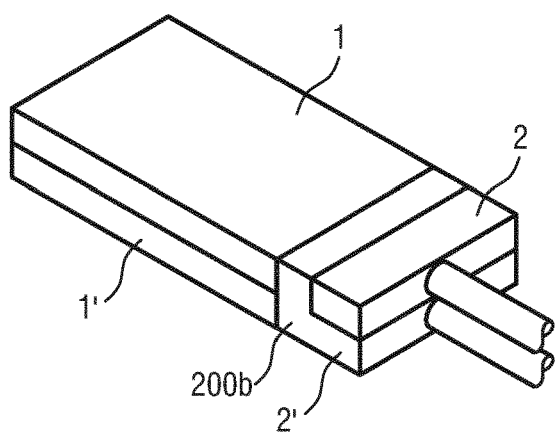

The connection unit 200 can be provided on the other side of the medical coupling units 1, 1' as shown in FIG. 8A. Alternatively, the connection unit 200a can be provided in between the medical coupling units 1, 1' and the medical sensors 2, 2' as shown in FIG. 8B. Alternatively, the connection unit 200b can be provided fixed to one of the medical coupling units 1' and one of the medical sensors 2' (or to an adapter) as shown in FIG. 8C.

Figure 9A:
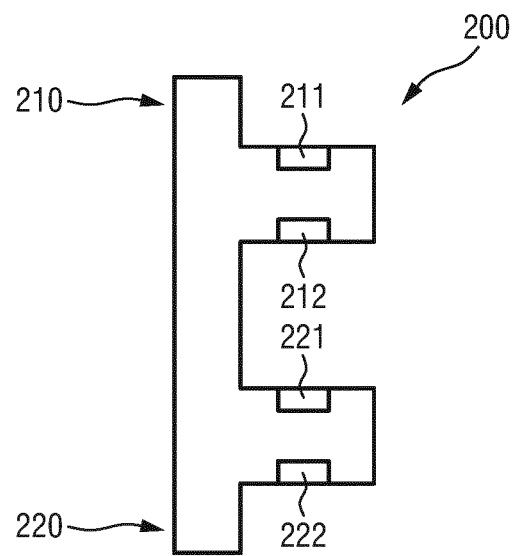
FIGS. 9A and 9B show schematic diagrams of two embodiments of the connection unit.
Figure 9B:
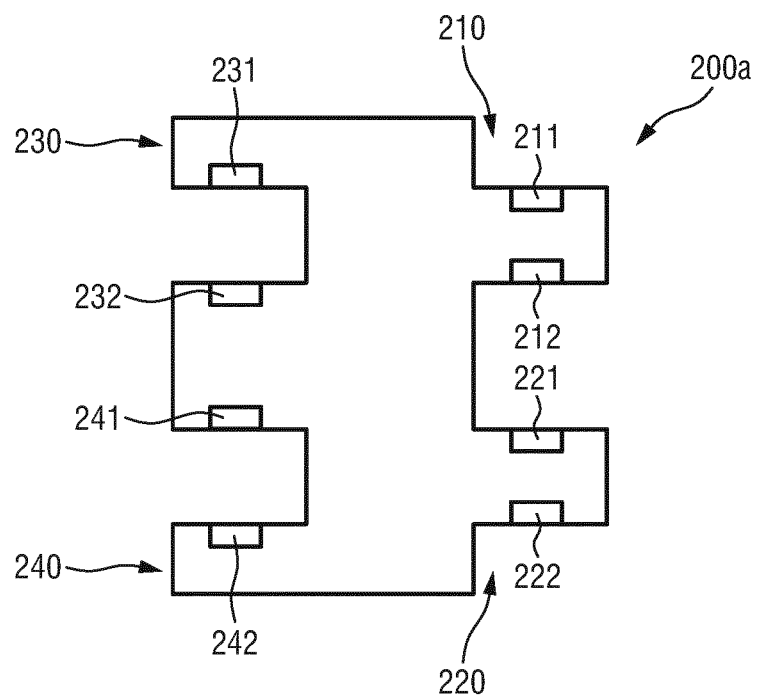

FIG. 9 shows a schematic diagram of a side view of the connection unit 200 (FIG. 9A) and the connection unit 200a (FIG. 9B).

The connection unit 200 shown in FIG. 9A comprises a first coupling-side connector 210 including a plurality of coupling-side electrical contacts 211, 212 for contacting a plurality of electrical contacts of a first coupling-side connector of a first medical coupling unit and a second coupling side connector 220 including a plurality of coupling-side electrical contacts 221, 222 for contacting a plurality of electrical contacts of a second coupling-side connector of a second medical coupling unit. In this embodiment the first coupling-side connector 210 and the second coupling-side connector 220 are arranged on top of each other and are configured as male connectors. Their relative arrangement can also be different, e.g. side by side, and female connectors may also be used instead.

The connection unit 200a shown in FIG. 9B additionally comprises a first sensor-side connector 230 including a plurality of sensor-side electrical contacts 231, 232 for contacting a plurality of electrical contacts of a first sensor-side connector of a first medical sensor unit and a second sensor side connector 240 including a plurality of sensor-side electrical contacts 241, 242 for contacting a plurality of electrical contacts of a second sensor-side connector of a second medical sensor unit. Hereby, the first sensor-side connector 230 is arranged opposite the first coupling-side connector 210 and the second sensor-side connector 240 is arranged opposite the second coupling-side connector 220. The first sensor-side connector 230 and the second sensor-side connector 240 are configured as female connectors, but may also be configured as male connectors instead.

The proposed adapter may also be configured such that signals from an auxiliary transducer to e.g. extra ECG leads are replaced. For instance, a 3-lead ECG system could include another transducer (e.g. an electronic thermometer, accelerometer, etc.) in the same connector. When the patient is temporarily upgraded to a 12-lead ECG, the wires associated with the auxiliary transducer can be replaced by the extra 7 ECG electrodes using the proposed adapter.

In another embodiment the proposed adapter may be used to extend a single measurement element (e.g. an electronic thermometer) with additional measurement elements of the same type. For instance, a thermometer may be extended with a second and third thermometer by using a 1→3 type adapter. This could be avoided by shifting pinning group positions in the adapter. For instance, assuming the connector can handle four thermometers on pinning group positions 1, 2, 3 and 4. First thermometer is connected to pinning group 1. The adapter may then configured such that it maps/shifts sensor-side pinning groups 1, 2, 3 to coupling-side pinning groups 2, 3, 4 and puts the extra thermometer on group 1. This way a single-type adapter can be used to added a second, or a third, or a fourth thermometer. Software could hide the pin remapping to avoid confusion for the user.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An adapter to couple with a medical coupling unit and a medical sensor that are configured to be coupled to transmit electrical signal between them, said adapter comprising:
    an adapter coupling unit comprising:
        a coupling-side connector configured to fit with a coupling-side connector of the medical coupling unit and including a plurality of coupling-side electrical contacts to contact a plurality of electrical contacts of the coupling-side connector of the medical coupling unit, and
        a sensor-side connector configured to fit with a sensor-side connector of the medical sensor and including a plurality of sensor-side electrical contacts to contact a plurality of electrical contacts of the sensor-side connector of the medical sensor, allowing the adapter coupling unit to be mechanically coupled between the medical coupling unit and the medical sensor, wherein the coupling-side connector is mechanically and electrically configured like the sensor-side connector of the medical sensor and the sensor-side connector is mechanically and electrically configured like the coupling-side connector of the medical coupling unit allowing a coupling of the medical coupling unit and the medical sensor either directly or via the adapter,
    two or more wires fixedly connected to the adapter coupling unit to couple two or more sensor elements with the adapter coupling unit to transmit electrical signal from the two or more sensor elements to the adapter coupling unit, wherein the two or more sensor elements are separate from the medical sensor, and
    connection circuitry within the adapter coupling unit to connect said sensor-side electrical contacts and said two or more wires with said coupling-side electrical contacts allowing signal transmission from the medical sensor and the two or more sensor elements coupled to the adapter coupling unit to the medical coupling unit.

2. The adapter as claimed in claim 1, wherein said plurality of coupling-side electrical contacts comprises a plurality of first coupling-side electrical contacts in or on a first surface and a plurality of second coupling-side electrical contacts in or on a second surface opposite the first surface and wherein said plurality of sensor-side electrical contacts comprises a plurality of first sensor-side electrical contacts in or on a third surface and a plurality of second sensor-side electrical contacts in or on a fourth surface opposite the first surface.

3. The adapter as claimed in claim 1,
    wherein said plurality of coupling-side electrical contacts are configured as male contacts and said plurality of sensor-side electrical contacts are configured as female contacts, or
    wherein said plurality of coupling-side electrical contacts are configured as female contacts and said plurality of sensor-side electrical contacts are configured as male contacts.

4. The adapter as claimed in claim 1, further comprising protection circuitry, the protection circuitry comprising one or more sidactors and/or protection resistors coupled between the two or more sensor elements and the one or more coupling-side electrical contacts.

5. The adapter as claimed in claim 1, wherein said adapter coupling unit has a flat or cylindrical shape.

6. The adapter as claimed in claim 1, wherein said coupling-side connector and/or said sensor side connector comprises one or more mechanical keying elements.

7. The adapter as claimed in claim 1, wherein said adapter coupling unit comprises communication circuitry to communicate with the medical coupling unit and/or a medical sensor.

8. The adapter as claimed in claim 1, wherein said two or more wires extend from two side surfaces of the adapter coupling unit.

9. The adapter as claimed in claim 8, wherein said two or more wires extend from two side surfaces of the adapter coupling unit at an angle of 90° with respect to the respective side surface.

10. The adapter as claimed in claim 8, wherein said adapter coupling unit is larger in width than the sensor-side connector of the medical sensor and wherein said two or more wires extend from a protruding portion of the adapter coupling unit, which protrudes beyond the sensor-side connector, in a direction of the sensor-side connector.

11. A connection unit configured to connect two or more medical coupling units with two or more medical sensors for to transmit electrical signal between them, said connection unit comprising:
   a first coupling-side connector including a plurality of coupling-side electrical contacts to contact a plurality of electrical contacts of a first coupling-side connector of a first medical coupling unit,
   a second coupling side connector including a plurality of coupling-side electrical contacts to contact a plurality of electrical contacts of a second coupling-side connector of a second medical coupling unit,
   a first sensor-side connector including a plurality of sensor-side electrical contacts to contact a plurality of electrical contacts of a first sensor-side connector of a first medical sensor unit,
   a second sensor side connector including a plurality of sensor-side electrical contacts to contact a plurality of electrical contacts of a second sensor-side connector of a second medical sensor unit, and
   two or more wires fixedly connected to one or more side surfaces of the connection unit to couple two or more sensor elements with the connection unit to transmit electrical signal from the two or more sensor elements to the connection unit, wherein the two or more sensor elements are separate from the first and second medical sensor units, and
   wherein the coupling-side connectors are mechanically and electrically configured like the sensor-side connectors of the medical sensor units and the sensor-side connectors are mechanically and electrically configured like the coupling-side connectors of the medical coupling units allowing a coupling of the medical coupling units and the medical sensor units either directly or via the connection unit.

12. The connection unit as claimed in claim 11, wherein said first coupling-side connector and said second coupling-side connector are arranged on top of each other.

13. The connection unit as claimed in claim 11, wherein the first sensor-side connector is arranged opposite the first coupling-side connector and the second sensor-side connector is arranged opposite the second coupling-side connector.

* * * * *